(12) United States Patent
Van Bommel et al.

(10) Patent No.: US 11,918,716 B2
(45) Date of Patent: Mar. 5, 2024

(54) MULTIFUNCTIONAL LUMINAIRE

(71) Applicant: SIGNIFY HOLDING B.V., Eindhoven (NL)

(72) Inventors: Ties Van Bommel, Horst (NL); Robert Jacob Pet, Waalre (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 18/031,924

(22) PCT Filed: Oct. 8, 2021

(86) PCT No.: PCT/EP2021/077823
§ 371 (c)(1),
(2) Date: Apr. 14, 2023

(87) PCT Pub. No.: WO2022/078882
PCT Pub. Date: Apr. 21, 2022

(65) Prior Publication Data
US 2023/0381363 A1 Nov. 30, 2023

(30) Foreign Application Priority Data
Oct. 15, 2020 (EP) ..................................... 20201943

(51) Int. Cl.
*F21V 33/00* (2006.01)
*A61L 9/20* (2006.01)
(Continued)

(52) U.S. Cl.
CPC . *A61L 9/20* (2013.01); *F21S 8/06* (2013.01); *F21V 7/0033* (2013.01); *F21V 7/10* (2013.01); *F21V 33/0064* (2013.01); *A61L 2209/111* (2013.01); *A61L 2209/12* (2013.01); *F21Y 2113/10* (2016.08); *F21Y 2115/10* (2016.08)

(58) Field of Classification Search
CPC .. A61L 9/20; A61L 2209/111; A61L 2209/12; F21S 8/06; F21V 7/0033; F21V 7/10; F21V 33/0064; F21Y 2113/10; F21Y 2115/10
See application file for complete search history.

(56) References Cited

U.S. PATENT DOCUMENTS 11,369,704 B2 * 6/2022 Winslow ................... A61L 2/26
2007/0053188 A1 3/2007 New et al.
(Continued)

FOREIGN PATENT DOCUMENTS

CN 108506829 A 9/2018
EP 3660385 A1 6/2020
(Continued)

*Primary Examiner* — Evan P Dzierzynski

(57) ABSTRACT

There is provided a luminaire (100) comprising: a first type light source (110) configured to emit visible light (111), the first type light source having a visible light main intensity peak (112) having a maximum intensity (114) in a first direction (116) from the luminaire; a second type light source (120) configured to emit ultraviolet, UV, light (121), the second type light source having a UV light main intensity peak (122) having a maximum intensity (124) in a, transverse, second direction (126). There is also provided a lighting system comprising a plurality of luminaires (100).

13 Claims, 7 Drawing Sheets

(51) Int. Cl.
*F21S 8/06* (2006.01)
*F21V 7/00* (2006.01)
*F21V 7/10* (2006.01)
F21Y 113/10 (2016.01)
F21Y 115/10 (2016.01)

(56) References Cited

U.S. PATENT DOCUMENTS

| | | | |
|---|---|---|---|
| 2012/0199005 A1* | 8/2012 | Koji | F21V 17/06 |
| | | | 96/224 |
| 2015/0335246 A1 | 11/2015 | Rains, Jr. et al. | |
| 2018/0010759 A1* | 1/2018 | Schoemer | B60Q 1/2607 |
| 2018/0180226 A1 | 6/2018 | Van Bommel et al. | |
| 2019/0091358 A1 | 3/2019 | Liao et al. | |
| 2019/0292315 A1 | 9/2019 | Niemiec et al. | |
| 2019/0333896 A1* | 10/2019 | Song | H01L 25/075 |
| 2020/0230271 A1* | 7/2020 | Choi | F21V 23/0464 |

FOREIGN PATENT DOCUMENTS

| | | |
|---|---|---|
| KR | 20150024717 A | 3/2015 |
| KR | 101535242 B1 | 7/2015 |

\* cited by examiner

MULTIFUNCTIONAL LUMINAIRE

CROSS-REFERENCE TO PRIOR APPLICATIONS

This application is the U.S. National Phase application under 35 U.S.C. § 371 of International Application No. PCT/EP2021/077823, filed on Oct. 8, 2021, which claims the benefit of European Patent Application No. 20201943.6, filed on Oct. 15, 2020. These applications are hereby incorporated by reference herein.

FIELD OF THE INVENTION

The present invention relates to luminaires comprising sources of both white light and ultraviolet, UV, light.

BACKGROUND OF THE INVENTION

UV light, i.e. electromagnetic radiation with a wavelength in the range from 10 to 400 nm, is known to possess germicidal qualities. Exposure to UV light may break down the DNA of microorganisms such as bacteria and viruses, in turn preventing them from replicating and causing disease. UV light, e.g. from the UV-C sub-range with a wavelength between 100 and 280 nm, may be effectively employed for disinfecting various surfaces and substances. As such, UV light may be utilized for applications such as drinking water purification, food processing, sterilization of medical equipment, etc. As a response to pathogenic outbreaks involving airborne microorganisms it would be beneficial to employ UV light for disinfecting air at locations where the transmission of such microorganisms is believed to occur. However, this may involve operating UV light sources in environments with human activity and humans would then be at risk of being irradiated with UV light. Under most conditions this would be considered health averse and sometimes even dangerous. As such it is clear that there is opportunity for improvement within the technical field.

SUMMARY OF THE INVENTION

It is an object of the present invention to overcome the problems in the prior art and provide a human safe solution for air disinfection by UV light exposure.

According to a first aspect, a luminaire is provided. The luminaire comprises a first type light source configured to emit visible light. The first type light source has a visible light main intensity peak with a maximum intensity in a first direction from the luminaire. The luminaire further comprises a second type light source configured to emit ultraviolet, UV, light. The second type light source has a UV light main intensity peak with a maximum intensity in a, transverse, second direction.

The concept of a light main intensity peak may be understood in regard to an angular distribution of electromagnetic radiation radiating out from a center of a light source. The angular range with the largest photon intensities may be understood as corresponding to a light main intensity peak. A maximum intensity may be understood as corresponding to a peak intensity value of the associated light main intensity peak.

The first direction may be understood as a downward direction from a ceiling towards a floor of a room in which the luminaire is arranged. The first direction may alternatively be understood as an arbitrary direction between two walls confining a volume or a room in which the luminaire is arranged. The second direction may be understood as transverse relative to the first direction or as a direction substantially perpendicular to the first direction.

An advantageous effect of the first aspect may be that potentially harmful UV light may be directionally emitted and made to only exist in parts of a room, in which the luminaire is arranged, where humans are at least not meant to be. By emitting UV light in the transverse direction, a substantially horizontal blanket of UV light may be formed. The blanket may be parallel to e.g. the ceiling or floor of the room wherein the luminaire is arranged. Due to air circulating around within the room such a horizontal blanket of UV light may disinfect a larger portion of the air within the room than that which is directly irradiated. This may enable disinfection of most air within the room, and its connected surroundings, without placing humans directly in harm's way. At the very least, air within the room may be disinfected to some extent with less direct UV light irradiating any human occupants present within the room.

The luminaire may further function as a lighting fixture which enables co-utilization of at least some of the structural and electrical components such as e.g. housing and wiring. The multifunctional luminaire may further be more space efficient as lighting fixtures generally are a necessary feature for a lot of different types of rooms, of course dependent on the specific purpose of the room in question.

The first direction may be a downward direction aligned with a vector of gravitational acceleration. The vector of gravitational acceleration may be a understood as a being a gravitational acceleration vector of a celestial body, e.g. Earth, on which the luminaire is arranged or located.

The UV light main intensity peak may be at an angle $\theta$ in a range from 80 to 130 degrees, more preferably in a range from 85 to 120 degrees, most preferably in a range from 88 to 110 degrees, with respect to the visible light main intensity peak.

The angle $\theta$ may be understood as being relative to the downward direction. In general, a transverse angle $\theta$ which is slightly more directed away from the downward direction is favorable for safety reasons. UV light directed from a luminaire towards a ceiling is generally safer than UV light directed from a luminaire towards a floor as such UV light would be less likely to directly irradiate humans in a room defined by said floor and ceiling. An advantage of irradiating more of the air between the luminaire and the ceiling, essentially air above the luminaire, may be that air will be more potently disinfected due to the longer time of exposure to UV light.

The luminaire may comprise an optical element for collimating the UV light, according to a cartesian coordination system having x, y and z vectors, wherein the vector z is in the first direction. The vector z may alternatively be in a direction oppositely oriented to the first direction. The x and y vectors may be understood as directions transversal relative to the first direction. A horizontal blanket of UV light may be understood to correspond to a plane formed by the x and y vectors. The x, y, and z vectors may be understood as spatial axes in a three-dimensional space.

A full width half maximum, FWHM, of the UV light main intensity peak in the z-direction may be less than 10 degrees, more preferably less than 5 degrees, most preferably less than 3 degrees. This type of FWHM may be understood as being relative to the angular distribution of light. The FWHM may be understood as a measure of how "wide" the UV light main intensity peak may be in a direction corresponding to the vertical direction, the first direction, or the z-vector. A smaller FWHM corresponds to a thinner UV light main intensity peak. By having a smaller angular FWHM a more discrete horizontal blanket of UV light may be advantageously formed.

The luminaire may comprise a plurality of second type light sources. The plurality of second type light sources may be distributed at a plurality of transversal sides of the luminaire.

The plurality of sides of the luminaire may alternatively be understood as horizontal or lateral sides of the luminaire. An advantage of having a plurality of second type light sources and/or distributing these along a plurality of sides of the luminaire may be that a more continuous blanket of UV light may be formed. This may furthermore enable a more even UV light blanket coverage across a room in which the luminaire is arranged. In turn, this may also lead to an improved disinfection of the air in the room as less air may be able to slip though or past the blanket of UV light and thus being exposed to the disinfecting UV light.

The luminaire may be configured to suspend from a ceiling by a suspension arrangement. As such, the luminaire may be arranged in a room and effectively disinfect air within the room. The luminaire may preferably and advantageously be arranged more proximate to the ceiling than to a floor of such a room. This may be advantageous as it effectively creates a larger relatively safe volume within the room for humans to occupy.

The luminaire may further comprise a sensor. The sensor may e.g. be a UV light sensor that may aid in determining the intensity of output UV light and its distribution within the room. This may in turn be favorable for determining if the room is safe for humans to occupy and/or which parts of the room may be safe for humans to occupy. This should not be considered as excluding other sensor types as presented in this disclosure.

The luminaire may further comprise a controller configured to control an intensity of UV light emitted from the second type light source based on an output from the sensor.

By such a controller, the intensity of output UV light, and its distribution, may be controlled to be continuous and/or within safe levels. This may in turn be favorable for keeping the room safe for humans to occupy.

The UV light main intensity peak maximum intensity has a wavelength $\lambda$ in the UV-C range from 100 to 280 nm, more preferably in a range from 230 to 280 nm. UV light with a wavelength $\lambda$ within the preferred ranges may possess potent germicidal attributes, advantageous for disinfection applications.

The first type light source may be a solid-state light source such as a light-emitting diode, LED, and/or a laser diode. The second type light source may be a solid-state light source such as a LED and/or a laser diode. Such light sources may operate and emit light more efficiently than traditional types of light sources. A laser diode light source may emit UV light in a more controlled and discrete manner. The horizontal blanket of UV light may be more precisely formed if the second type light source is laser-based. As such, the horizontal blanket may advantageously be made thinner.

The luminaire may further comprise a reflector frame forming at least a part of a perimeter of an inner space essentially extending in an x-y plane. The x-y plane may be according to a cartesian coordinate system having x, y, and z vectors, wherein the vector z is in the first direction. The second type light source may be arranged to emit UV light into said inner space in plane with said x-y-plane. The UV light main intensity peak may have its maximum intensity in a direction towards a remotely arranged location across said inner space, at said location said UV light is:
  i) absorbed by a beam dump; or
  ii) reflected by a first part of the reflector frame back across said inner space to either a second part of the reflector frame or to a beam dump; or
  iii) reflected multiple times back and forth from said first part to said second part and from said second part to further parts of the reflector frame, optionally finally being reflected towards said beam dump.

Such a setup may be beneficial for effectively broadening the second type light source laser beam in a substantially horizontal, transversal, or lateral plane, in plane with the x-y plane. This may aid in forming the horizontal blanket of UV light. The beam dump may be understood as comprising material or surfaces configured or adapted to absorb UV light.

The second type of light source may be arranged in an aperture of the reflector frame. As such, the second type light source may be less obstructive for UV light reflecting within the inner space of the reflector frame. This may provide additional reflection area for more efficient recycling of the UV light.

The beam dump may be arranged in a consecutive manner above and/or below the reflector frame in the z-direction. The beam dump is thereby configured to absorb UV light that is spread out far enough in the z-direction. As such, a horizontal blanket of UV light may be formed in, or aligned with, the x-y plane.

The reflector frame is an open or closed ring-shaped reflector frame, wherein the ring-shaped reflector frame has a circular, an elliptical, or a polygonal shape, and wherein the reflector frame comprises two oppositely arranged sub-reflectors on either side of the inner space. The different sub-reflectors may be understood as the first and second parts of the reflector frame.

An advantage of an open ring-shaped reflector frame may be that the opening may be utilized for emitting light out into the surroundings of the luminaire. Vertical slit or circular apertures through the reflector frame may be utilized for the same purpose of emitting light out into the surroundings.

According to a second aspect, a lighting system comprising a plurality of luminaires according to the first aspect. The plurality of luminaires are arranged such that the UV light main intensity peaks of the plurality of luminaires substantially overlap.

An advantage of having a plurality of luminaires arranged together in a system may be that a more continuous blanket of UV light may be formed. This may furthermore enable a more even UV light blanket coverage across a room in which the luminaire is arranged. In turn, this may also lead to an improved disinfection of the air in the room as less air may be able to slip though or past the blanket of UV light and thus being exposed to the disinfecting UV light.

At least a sub portion of the plurality of luminaires may comprise a sensor e.g. a UV light sensor. A sensor of a specific luminaire in the sub portion may be configured to measure UV light of a neighboring luminaire.

The specific luminaire may comprise a controller. The controller may be configured to control an intensity of UV light emitted from the second type light source of the specific luminaire. The controller may be configured to control an intensity of UV light emitted from the second type light source of the neighboring luminaire based on an output from the sensor.

In general, the above system embodiments may provide similar advantages as those discussed in conjunction with the corresponding or similar embodiments of the first aspect.

A further scope of applicability of the present invention will become apparent from the detailed description given below. However, it should be understood that the detailed description and specific examples, while indicating preferred embodiments of the invention, are given by way of illustration only, since various changes and modifications within the scope of the invention will become apparent to those skilled in the art from this detailed description.

Hence, it is to be understood that this invention is not limited to the particular component parts of the device described as such device may vary. It is also to be understood that the terminology used herein is for purpose of describing particular embodiments only, and is not intended to be limiting. It must be noted that, as used in the specification and the appended claim, the articles "a," "an," and "the," are intended to mean that there are one or more of the elements unless the context clearly dictates otherwise. Thus, for example, reference to "a lamp" or "the lamp" may include several devices, and the like. Furthermore, the words "comprising", "including", "containing" and similar wordings does not exclude other elements or steps.

BRIEF DESCRIPTION OF THE DRAWINGS

The above and other aspects of the present invention will now be described in more detail, with reference to the appended drawings showing embodiments of the invention. The figures should not be considered limiting the invention to the specific embodiment; instead they are used for explaining and understanding the invention.

As illustrated in the figures, the sizes of layers and regions are exaggerated for illustrative purposes and, thus, are provided to illustrate the general structures of embodiments of the present invention. Like reference numerals refer to like elements throughout.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled person.

Figure 1:
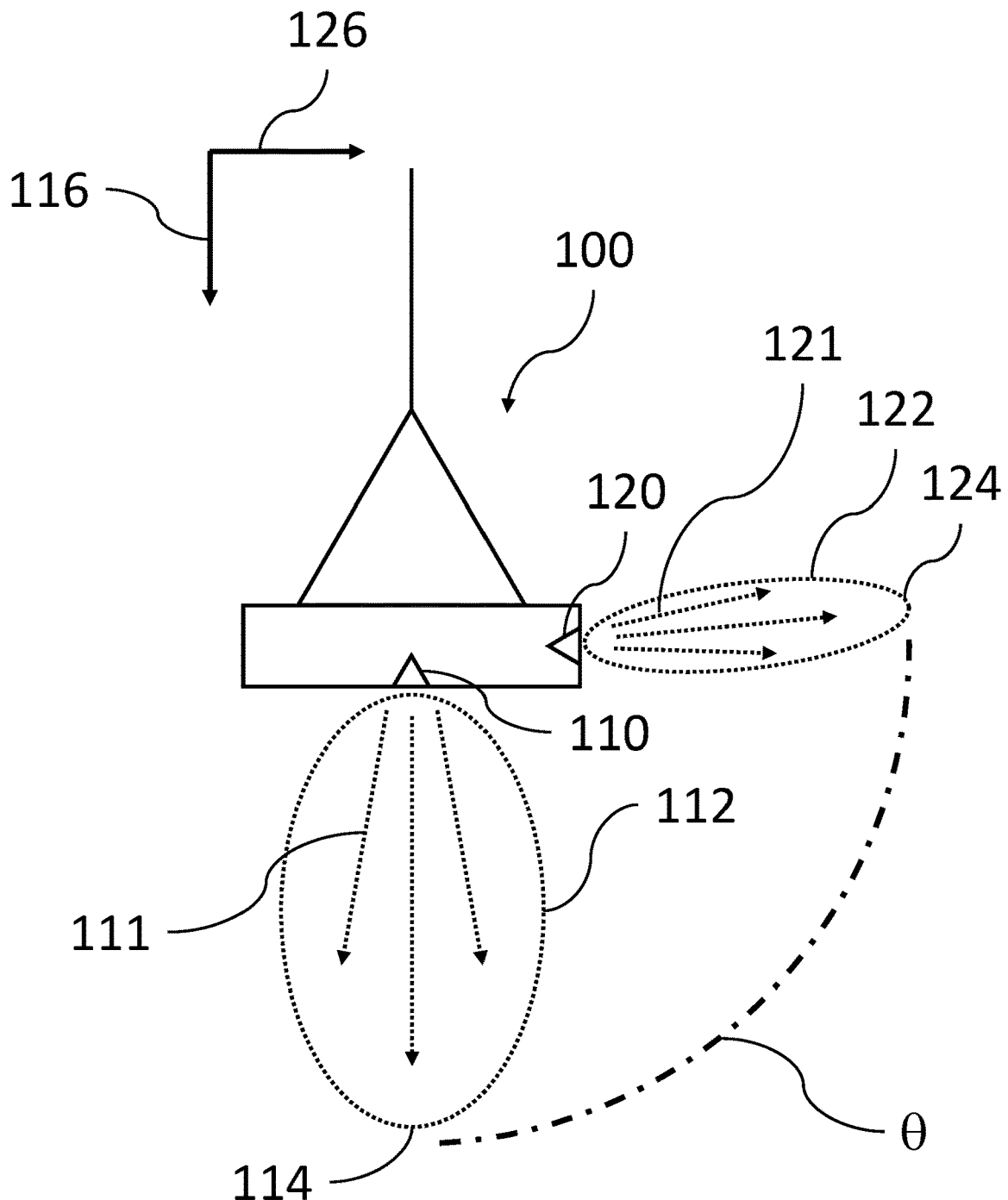
FIG. 1 shows a luminaire comprising a first type light source and a second type light source.

In FIG. 1 a luminaire 100 is schematically illustrated. The illustration may be considered a cross section or side-view illustration of the luminaire 100. The luminaire 100 may be housed within a luminaire housing that may be based on conventional general lighting luminaire housing. The luminaire 100 may be a suspended luminaire, as is indicated in FIG. 1. The luminaire 100 may be a ceiling suspended luminaire. The luminaire 100 may be a floor mounted/supported luminaire. The luminaire 100 may be a wall mounted/fixed luminaire.

The luminaire is shown to comprise a first type light source 110 and a second type light source 120. The first light source 110 being configured to emit visible light 111. The first type light source 110 having a visible light main intensity peak 112. The visible light main intensity peak 112 having a maximum intensity 114 in a first direction 116 from the luminaire 100. The first direction 116 being illustrated in FIG. 1 in relation to the luminaire 100. The first direction 116 may be a downward direction aligned with a vector of gravitational acceleration.

The second type light source 120 is configured to emit UV light 121. The second type light source 120 having a UV light main intensity peak 122. The UV light main intensity peak 122 having a maximum intensity 124 in a, relative to the first direction 116, transverse, second direction 126 from the luminaire 100. The second direction 126 being illustrated in FIG. 1 in relation to the luminaire 100.

FIG. 1 shows the UV light main intensity peak 122 being at an angle θ with respect to the visible light main intensity peak 112. The figure may be considered to show the angle θ being between the corresponding maximum intensities 124, 114 or being between corresponding average or median directions of the UV light main intensity peak 122 and the visible light main intensity peak 112. The angle θ may be in a range from 80 to 130 degrees, more preferably in a range from 85 to 120 degrees, most preferably in a range from 88 to 110 degrees. The angle θ may be substantially 90 degrees.

The first type light source 110 may comprise or be a solid-state light source such as a LED and/or a laser diode. The first type light source 110 may comprise or be a nitride semiconductor-based LED. The first type light source 110 may be based on a blue light emitting LED. The first type light source 110 may comprise gallium nitride, indium gallium nitride, and/or aluminum gallium nitride semiconductor materials. The first type light source 110 may comprise lenses, apertures, and/or coatings for modulating and/or spreading raw light emitted by an internal light source of the first type light source 110. The internal source may be a nitride-based LED and/or blue light emitting LED. The first type light source 110 may be configured to modulate raw emitted light, e.g. blue light, into white light. The first type light source 110 may comprise a phosphor-based coating. The first type light source 110 may be configured and/or adapted for general lighting. The first type light source 110 may be configured to emit wavelengths within the range from 380 to 740 nm, i.e. a visible spectrum of light. FIG. 1 shows the first type light source 110 being located on a bottom side of the luminaire 100.

The second type light source 120 may comprise or be a solid-state light source such as a LED and/or a laser diode. The second type light source 120 may comprise or be a nitride semiconductor-based LED. The second type light source 120 may comprise gallium nitride, indium gallium nitride, and/or aluminum gallium nitride semiconductor materials.

The second type light source 120 may comprise lenses, apertures, coatings, and/or filters for modulating raw UV light. The second type light source 120 may e.g. comprise a wavelength filter that may filter out more harmful wavelengths of UV light from the raw UV light that are not deemed necessary for the required disinfection or germicide application. A second type light source 120 being or comprising a laser diode may be configured to emit light with a wavelength of e.g. 405 nm. FIG. 1 shows the second type light source 120 being located on a transversal side of the luminaire 100. The luminaire 100 may comprise an optical element for collimating the UV light 121, according to a cartesian coordination system having x, y and z vectors, wherein the vector z is in the first direction 116.

The visible light main intensity peak 112 may be configured to directly and/or indirectly illuminate most or all of the luminaires 100 surroundings. An angular intensity FWHM for the visible light main intensity peak 112 may be relatively large, e.g. in the range from 90 to 180 degrees.

The UV light main intensity peak 122 may feature an angular intensity FWHM that is less than 10 degrees, more preferably less than 5 degrees, most preferably less than 3 degrees. The angular intensity FWHM is visualized as being confined in the z-direction in FIGS. 7*a-c*.

Figure 7A:
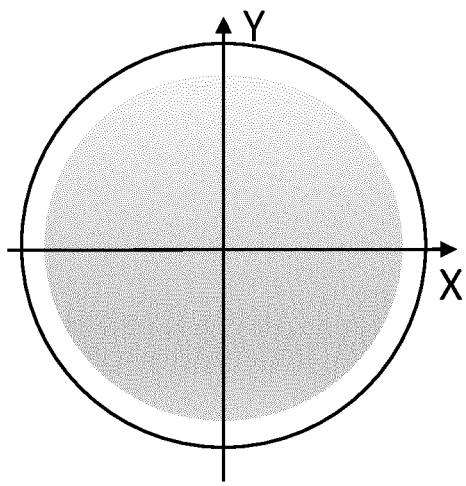
FIGS. 7A-C show examples of distribution of UV light from a second type light source.
Figure 7B:
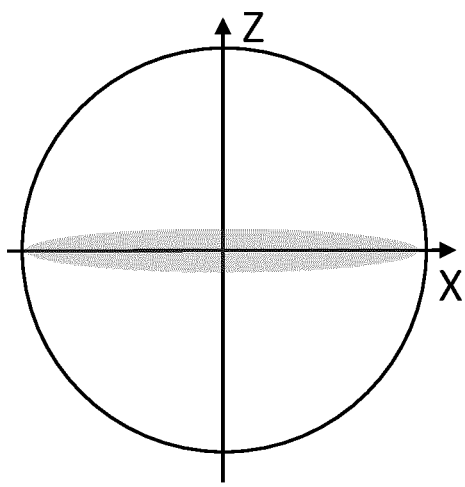
Figure 7C:
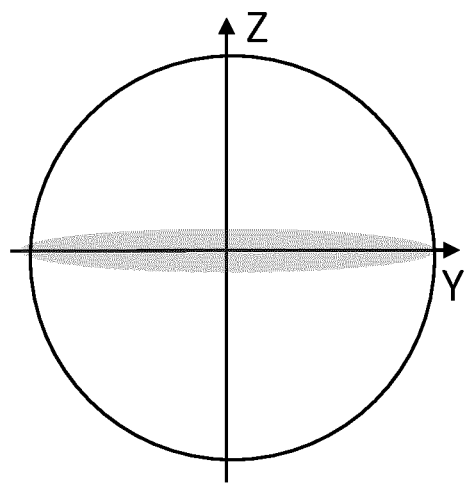

FIG. 7*a* shows possible omnidirectional distribution of the UV light main intensity peak 122 in the x-y plane from a second type light source 120. FIG. 7*b* shows the UV light main intensity peak 122 angular distribution in the x-z plane from a second type light source 120. FIG. 7*c* shows the UV light main intensity peak 122 angular distribution in the y-z plane from a second type light source 120. The FWHM of the UV light main intensity peaks in the x-z and y-z planes may be understood as being less than 10 degrees, 5 degrees, or 3 degrees, in the z-direction.

The UV light main intensity peak maximum intensity 124 may have a wavelength λ in the UV-C range from 100 to 280 nm, more preferably in a range from 230 to 280 nm. The UV-C range may generally be seen as a subrange of UV light. The wavelength λ range from 230 to 280 nm may generally be understood as the deep UV-C range.

The UV light main intensity peak maximum intensity 124 may have a wavelength λ in a range from 200 to 230 nm. This range may generally be understood as the far UV-C range. The UV light main intensity peak maximum intensity 124 may have a wavelength λ in a range from 207 to 222 nm. Wavelengths λ within these two latter ranges may be less harmful to humans than other wavelengths λ of UV light.

Figure 2:
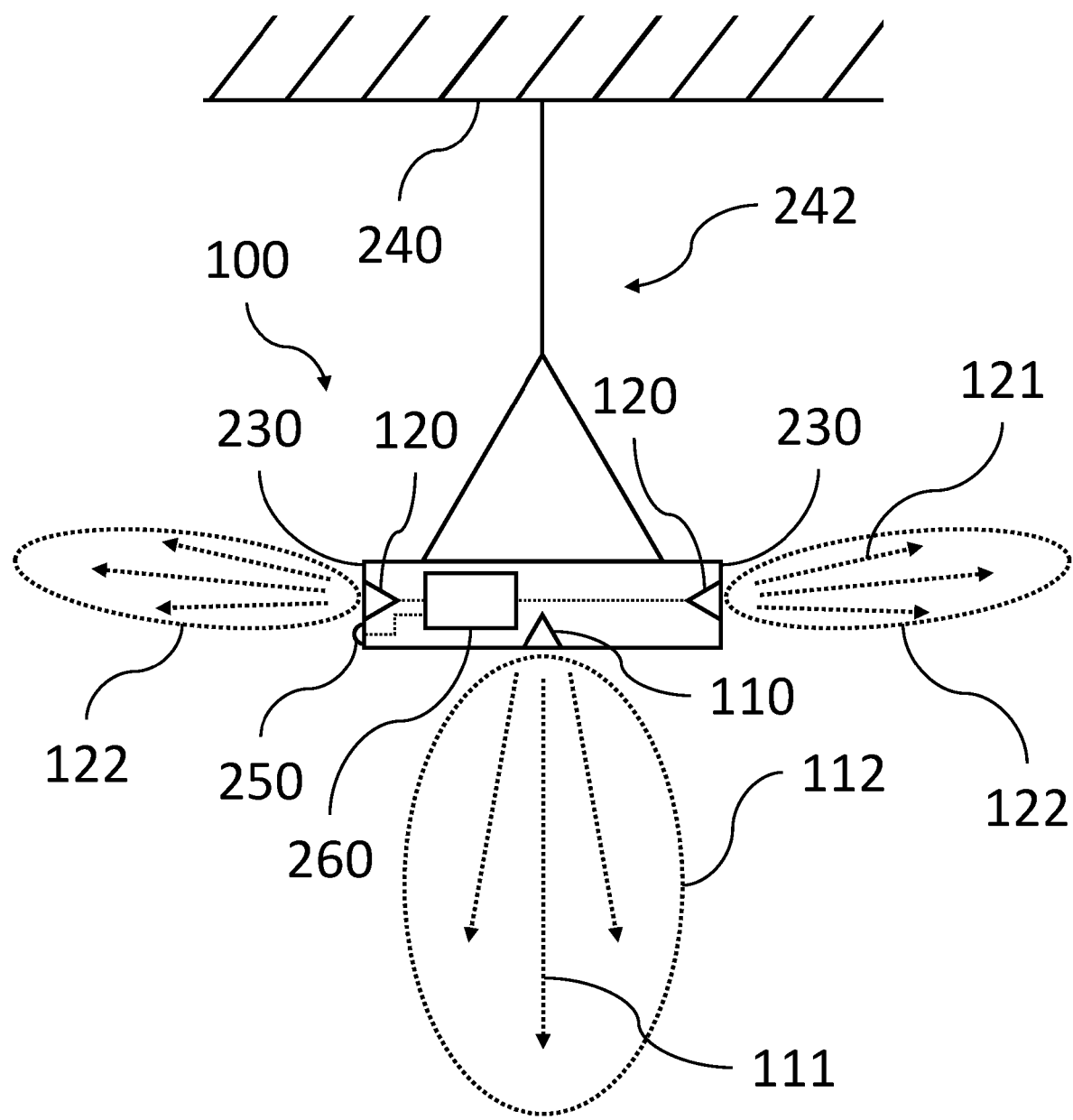
FIG. 2 shows a luminaire comprising a first type light source and a plurality of second type light sources.

In FIG. 2 a luminaire 100 is schematically illustrated similarly to how the luminaire 100 is illustrated in FIG. 1. The illustration may be considered a cross section or side-view illustration of the luminaire 100.

FIG. 2 shows the luminaire 100 comprising a plurality of second type light sources 120. The figure further shows the plurality of second type light sources 120 being distributed at a plurality of transversal sides 230 of the luminaire 100. Specifically, the figure shows two second type light source 120 being located at two opposite transversal sides 230 of the luminaire 100. The sides 230 of the luminaire 100 may be transversally oriented. In general, each side 230 of the luminaire 100 may hold at least one second type light source 120 each. The luminaire 100 may comprise an arbitrary number of sides 230. The luminaire 100 may e.g. comprise four sides 230. Correspondingly, the luminaire 100 may comprise four second type light sources 120. The transversal sides 230 may extend between an upper and a lower side of the luminaire 100. The upper side may face a ceiling. The lower side may face a floor. The upper side and/or the lower side may be parallel to a ceiling and/or a floor.

The luminaire 100 may alternatively be understood as being radially elongated in the transversal plane. As such, it may only comprise one transversal side 230 going around the circumference of the luminaire 100. In such embodiments, second type light sources 120 may be placed along the circumference of the luminaire 100.

FIG. 2 shows the luminaire 100 being configured to suspend from a ceiling 240 by a suspension arrangement 242. The ceiling 240 may be located directionally opposite to the first direction 116 relative the luminaire 100. This should however not be understood as a requirement as the luminaire 100 may be arranged in a desired location using a other means such as a post arrangement, instead being supported by a floor or other surfaces in the first direction 116. Lateral arrangement of the luminaire 100, e.g. by having it fixed directly or indirectly to a wall, provides further possible embodiments.

The luminaire 100 may be arranged at a distance D from the ceiling 240. The distance D may be at least 0.5 m, more preferably at least 1 m, most preferably at least 1.5 m. The reason for larger distances D is to have a larger volume of air above the luminaire 100 for circulation and treatment, i.e. disinfection and germicide. The luminaire 100 may suspend preferably at least 2 m above a ground i.e. a floor, more preferably at least 2.3 m above the ground, most preferably at least 2.5 m above the ground. The reason for this ensuring the safety of humans and mitigating the risks of unintended and potentially harmful irradiation with UV light.

FIG. 2 shows the luminaire 100 comprising a sensor 250. The sensor is shown located transversally on the luminaire 100, proximate to one of the second type light sources 120. The sensor 250 may be a UV light sensor. The sensor 250 may comprise a photocell type sensor, a photodiode type sensor, a photoresistor type sensor, a phototransistor type sensor, a charge-coupled device type sensor, an active-pixel type sensor, a complementary metal-oxide-semiconductor type sensor, or a photovoltaic cell type sensor. The sensor 250 may also be a distance sensor, a presence sensor, a motion sensor, a light sensor, etc. Essentially, the sensor 250 may be any type of suitable sensor.

FIG. 2 shows the luminaire 100 comprising a controller 260. The controller 260 may be configured to control an intensity of UV light emitted from the second type light source 120 based on an output from the sensor 250. E.g. if the sensor 250 senses a high intensity of UV light, the controller 260 may reduce the electrical power to the second type light source 120 or instruct it to otherwise reduce its output UV light intensity. The controller 260 may control shutters to reduce the output UV light intensity. The controller 260 may control actuators for redirecting the second type light source 120. The controller 260 may comprise circuitry as well as active and passive electronic components for performing the actions which it is configured for.

Figure 3:
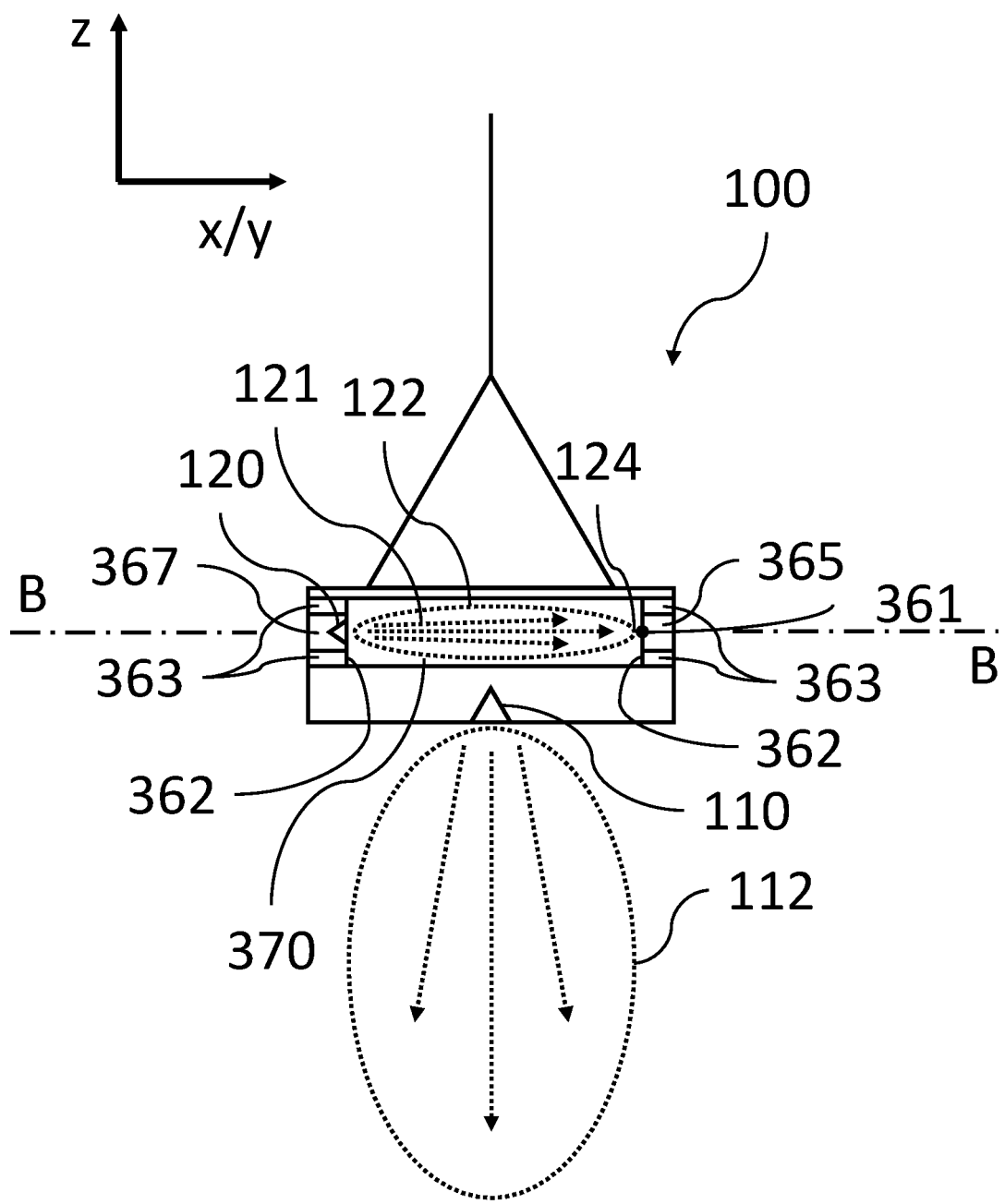
FIG. 3 shows a luminaire comprising a reflector frame.

FIG. 3 shows a side view cross section of the luminaire 100. The figure shows the luminaire 100 comprising a reflector frame 360 forming at least a part of a perimeter 362 of an inner space 370 essentially extending in an x-y plane. The x-y plane may be according to a cartesian coordination system having x, y, and z vectors, wherein the vector z is in the first direction 116. The second type light source 120 may be arranged to emit UV light 121 into said inner space 370 in plane with said x-y-plane. The UV light main intensity peak 122 has its maximum intensity 124 in a direction towards a remotely arranged location 361 across said inner space. At said location 361 said UV light is:
  i) absorbed by a beam dump 363; or
  ii) reflected by a first part 365 of the reflector frame 360 back across said inner space to either a second part 367 of the reflector frame 360 or to a beam dump 363; or
  iii) reflected multiple times back and forth from said first part 365 to said second part 367 and from said second part to further parts of the reflector frame 360, optionally finally being reflected towards said beam dump 363. The reflector frame 360 embodiments may be combined with a laser-based second type light source 120. The x-y plane may comprise the second direction 126. The x-y plane is indicated by the x/y axis in FIG. 3.

What happens to the UV light 121 at the remotely arranged location 361, i.e. items i), ii), and iii) may depend on the orientation of the reflector frame 360 and/or the second type light source 120 and/or the beam dump 363.

The second type of light source 120 may be is arranged in an aperture of the reflector frame 360. The beam dump 363 may be arranged in a consecutive manner above and/or below the reflector frame 360 in the z-direction. Essentially, light 121 not being reflected by the reflector frame 360 may be absorbed by the beam dump 363. The beam dump 363 may essentially be the same shape as the reflector frame 360, albeit being arranged offset in the z-direction. As shown in FIG. 3, the luminaire 100 may comprise a plurality of beam dump 363 features. In the figure, at least one beam dump 363 is shown to be arranged above the reflector frame 360 while at least one other beam dump 363 is shown to be arranged below the reflector frame 360.

The reflector frame 360 may be an open or closed ring-shaped reflector frame. The ring-shaped reflector frame may have a circular, an elliptical, or a polygonal shape. The reflector frame 360 may comprise two oppositely arranged sub-reflectors on either side of the inner space 370.

Figure 4:
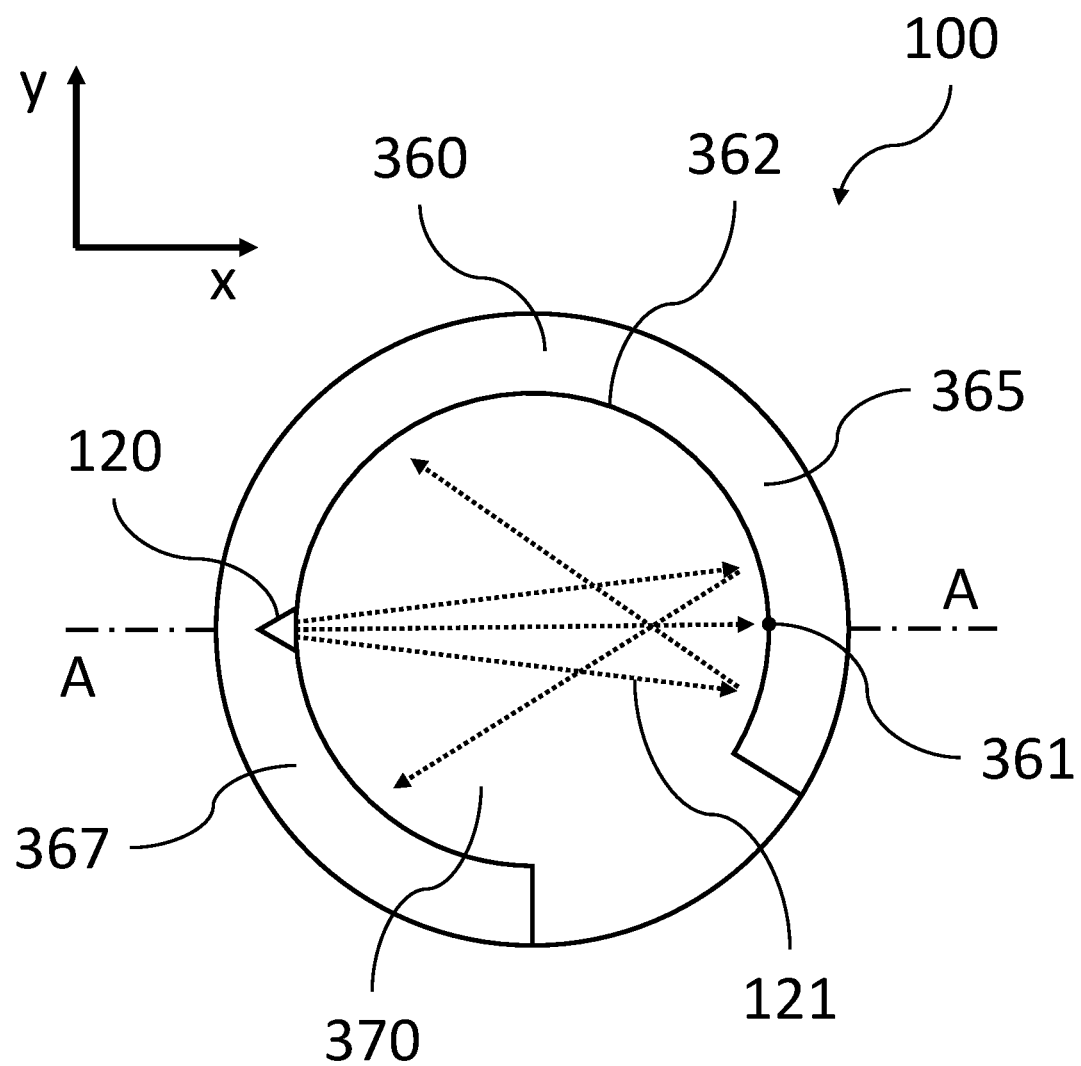
FIG. 4 shows a top view of a luminaire comprising a reflector frame.

FIG. 4 shows atop view cross section of the luminaire 100. The x-y axes indicate the figure how the figure shows a horizontal/lateral/transverse cross-section in the x-y plane. The figure shows the luminaire 100 comprising a reflector frame 360. The reflector frame 360 is an open ring-shaped reflector frame having a circular shape. The opening may be configured to let UV light 121 escape into the surroundings of the luminaire 100. The dotted arrows indicate how the UV light 121 may be reflected back and forth within the inner space 370.

FIGS. 3 and 4 may be understood as showing cross sections of the same luminaire 100. FIG. 3 shows a cross section along the plane A as indicated by the dash-dotted line in FIG. 4. Correspondingly, FIG. 4 shows a cross section along the plane B as indicated by the dash-dotted line in FIG. 3.

Figure 5:
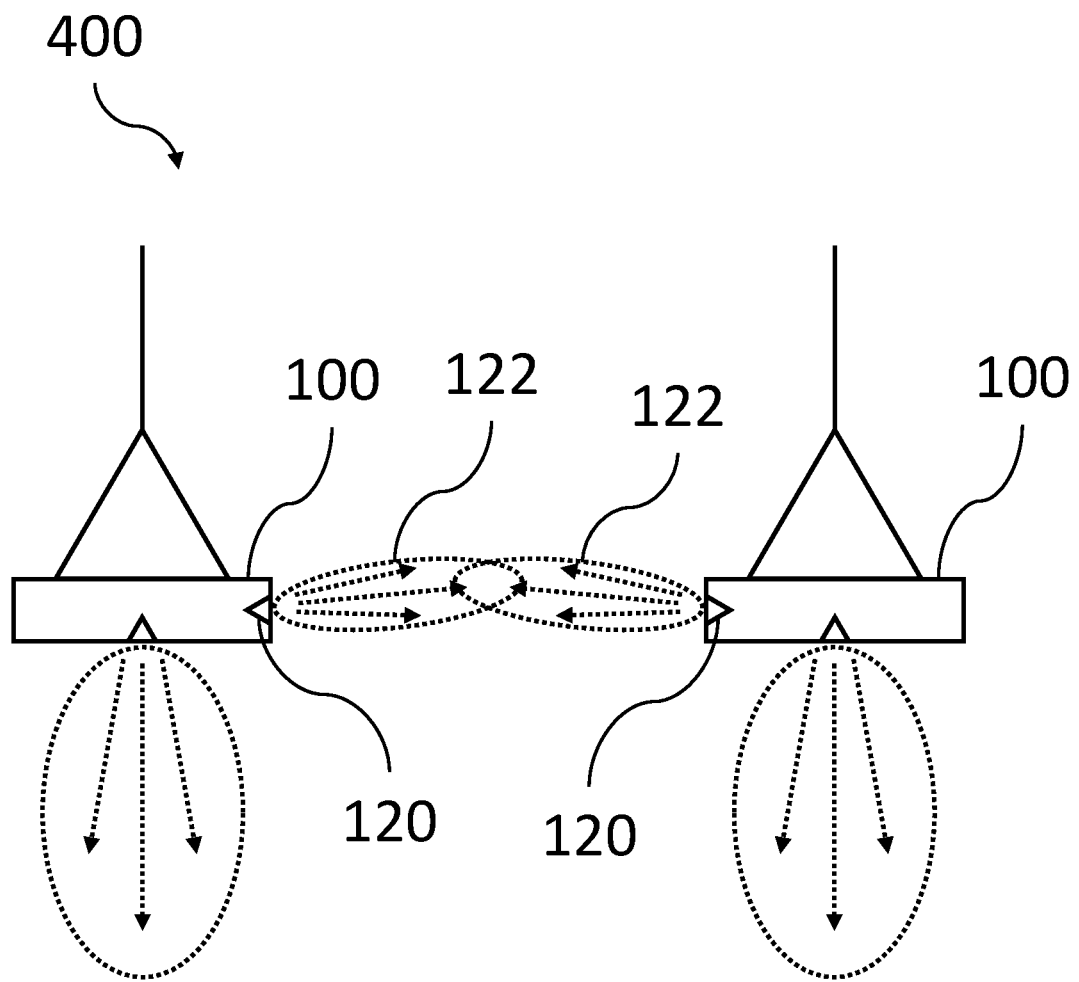
FIG. 5 shows a lighting system comprising a plurality of luminaires.

In FIG. 5 a lighting system 400 comprising a plurality of luminaires 100 is illustrated. The plurality of luminaires 100 are arranged such that the UV light main intensity peaks 122 of the plurality of luminaires 100 substantially overlap. The system 400 may be modular and comprise an arbitrary number of luminaires 100. The luminaires 100 of the lighting system 400 may be arranged at the same vertical level. This may lead to a thinner and more precise horizontal blanket of UV light. The luminaires 100 of the lighting system 400 may be arranged at different vertical levels. This may create a thicker horizontal blanket of UV light which may be more effective at disinfecting the air passing through the blanket.

Figure 6:
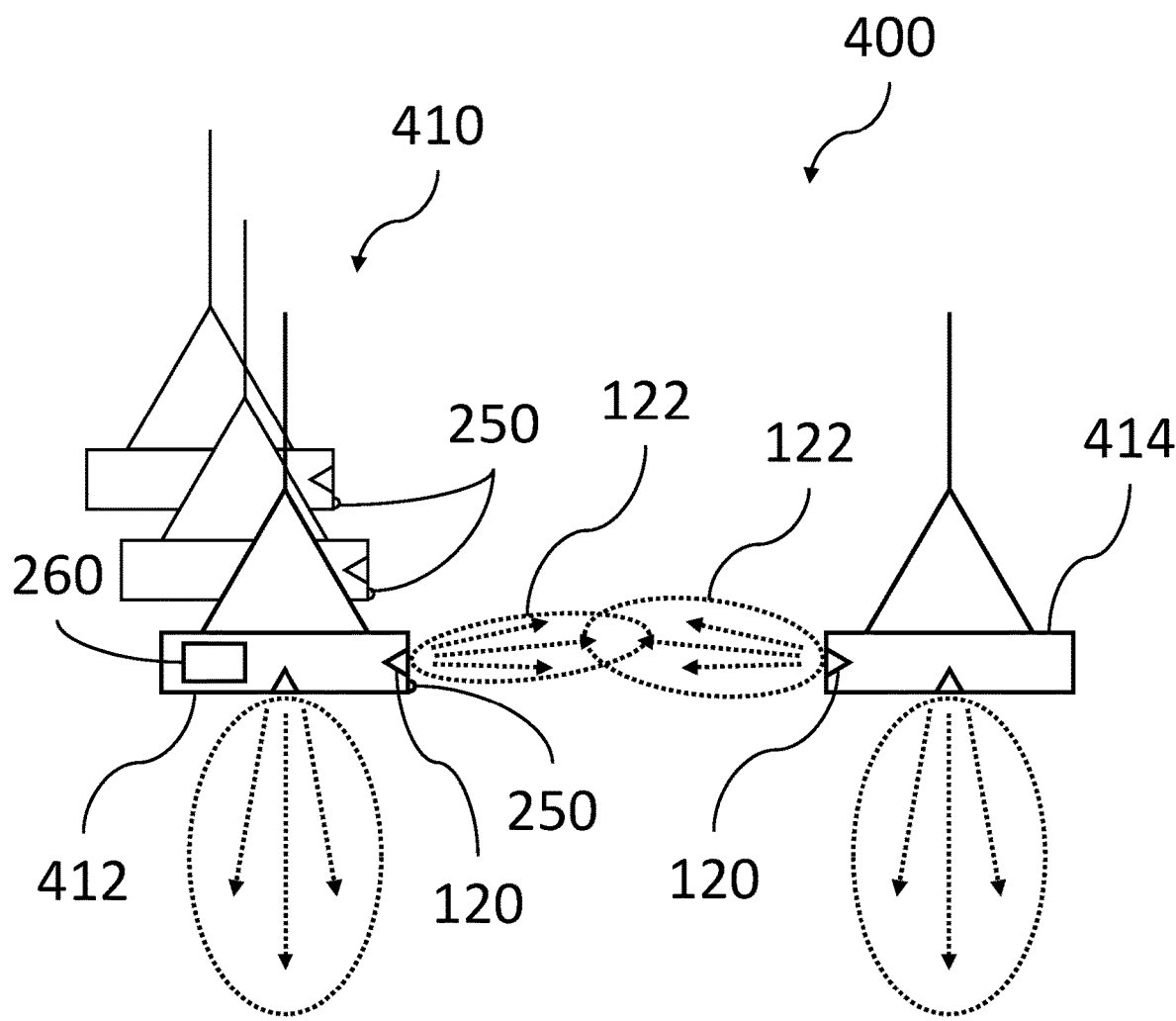
FIG. 6 shows a lighting system comprising a plurality of luminaires wherein a sub portion of the luminaires comprises at least a sensor.

In FIG. 6 at least a sub portion 410 of the plurality of luminaires 100 of the lighting system 400 comprise a sensor 250. A sensor 250 of a specific luminaire 412 in the sub portion 410 may be configured to measure UV light of a neighboring luminaire 414.

The specific luminaire 412 may comprise a controller 260 configured to control an intensity of UV light emitted from the second type light source 120 of the specific luminaire 412. The specific luminaire 412 may comprise a controller 260 configured to control an intensity of UV light emitted from the second type light source 120 of the neighboring luminaire 414 based on an output from the sensor.

The luminaire 100 and/or the system 400 may be primarily be arranged in indoor environments, e.g. rooms, without excluding its applicability for also outdoor environments and locations. The luminaire 100 and/or the system 400 may be arranged in rooms or locations where human activity occurs. The luminaire 100 and/or the system 400 may be arranged in rooms or locations where airborne microorganisms and pathogens are believed to exist in the air. The luminaire 100 and/or the system 400 may be arranged in rooms or locations where spread or transmission of airborne microorganisms and pathogens, and diseases based thereon, is believed to occur. The luminaire 100 and/or the system 400 may be arranged in rooms or locations where preventing spread or transmission of airborne microorganisms and pathogens is of high importance such as e.g. hospitals and other medical facilities, drug/food producing facilities, and/or laboratories. The luminaire 100 and/or the system 400 may be arranged in locations that see large numbers of human visitors, e.g. transit stations, airports, sports facilities, offices, retail stores, restaurants, auditoriums, etc.

Additionally, variations to the disclosed embodiments can be understood and effected by the skilled person in practicing the claimed invention, from a study of the drawings, the disclosure, and the appended claims.

The invention claimed is:

1. A luminaire comprising:
   a first type light source configured to emit visible light, the first type light source having a visible light main intensity peak having a maximum intensity in a first direction from the luminaire; and
   a second type light source configured to emit ultraviolet, UV, light, the second type light source having a UV light main intensity peak having a maximum intensity in a, transverse, second direction,
   wherein the first type light source and the second type light source is a solid-state light source such as a light-emitting diode, LED and/or a laser diode,
   said luminaire further comprising a reflector framed forming at least a part of a perimeter of an inner space essentially extending in an x-y plane, according to a cartesian coordination system having x, y, and z vectors, wherein the vector z is in the first direction, wherein the second type light source is arranged to emit UV light into said inner space in plane with said x-y-plane, wherein the UV light main intensity peak has its maximum intensity in a direction towards a remotely arranged location across said inner space, at said location said UV light is:
   i) absorbed by a beam dump; or
   ii) reflected by a first part of the reflector frame back across said inner space to either a second part of the reflector frame or to a beam dump; or
   iii) reflected multiple times back and forth from said first part to said second part and from said second part to further parts of the reflector frame, optionally finally being reflected towards said beam dump.

2. The luminaire according to claim 1, wherein the first direction is a downward direction aligned with a vector of gravitational acceleration.

3. The luminaire according to claim 1, wherein the UV light main intensity peak is at an angle θ in a range from 80 to 130 degrees, more preferably in a range from 85 to 120 degrees, most preferably in a range from 88 to 110 degrees, with respect to the visible light main intensity peak.

4. The luminaire according to claim 1, comprising an optical element for collimating the UV light, according to a cartesian coordination system having x, y and z vectors, wherein the vector z is in the first direction, wherein a full width half maximum, FWHM, of the UV light main intensity peak in the z-direction is less than 10 degrees, more preferably less than 5 degrees, most preferably less than 3 degrees.

5. The luminaire according to claim 1, wherein the luminaire comprises a plurality of second type light sources wherein the plurality of second type light sources are distributed at a plurality of transversal sides of the luminaire.

6. The luminaire according to claim 1, wherein the luminaire is configured to suspend from a ceiling by a suspension arrangement.

7. The luminaire according to claim 1 further comprising:
a sensor; and
a controller configured to control an intensity of UV light emitted from the second type light source based on an output from the sensor.

8. The luminaire according to claim 1, wherein the UV light main intensity peak maximum intensity has a wavelength $\lambda$ in the UV-C range from 100 to 280 nm, more preferably in a range from 230 to 280 nm.

9. The luminaire according to claim 8, wherein the second type of light source is arranged in an aperture of the reflector frame.

10. The luminaire according to claim 8, wherein the beam dump is arranged in a consecutive manner above and/or below the reflector frame in the z-direction.

11. The luminaire according to claim 8, wherein the reflector frame is an open or closed ring-shaped reflector frame, wherein the ring-shaped reflector frame has a circular, an elliptical, or a polygonal shape, and wherein the reflector frame comprises two oppositely arranged sub-reflectors on either side of the inner space.

12. A lighting system comprising a plurality of luminaires, each luminaire comprising:
a first type light source configured to emit visible light, the first type light source having a visible light main intensity peak having a maximum intensity in a first direction from the luminaire; and
a second type light source configured to emit ultraviolet, UV, light, the second type light source having a UV light main intensity peak having a maximum intensity in a, transverse, second direction,
wherein the plurality of luminaires are arranged such that the UV light main intensity peaks of the plurality of luminaires substantially overlap, wherein at least a sub portion of the plurality of luminaires comprises a sensor, wherein a sensor of a specific luminaire in the sub portion is configured to measure UV light of a neighboring luminaire, and wherein the specific luminaire comprises a controller configured to control an intensity of UV light emitted from the second type light source of the specific luminaire or an intensity of UV light emitted from the second type light source of the neighboring luminaire based on an output from the sensor.

13. The lighting system according to claim 12, wherein the first type light source and the second type light source is a solid-state light source such as a light-emitting diode, LED and/or a laser diode, and
wherein each luminaire, further comprising a reflector frame forming at least a part of a perimeter of an inner space essentially extending in an x-y plane, according to a cartesian coordination system having x, y, and z vectors, wherein the vector z is in the first direction, wherein the second type light source is arranged to emit UV light into said inner space in plane with said x-y-plane, wherein the UV light main intensity peak has its maximum intensity in a direction towards a remotely arranged location across said inner space, at said location said UV light is:
i) absorbed by a beam dump; or
ii) reflected by a first part of the reflector frame back across said inner space to either a second part of the reflector frame or to a beam dump; or
iii) reflected multiple times back and forth from said first part to said second part and from said second part to further parts of the reflector frame, optionally finally being reflected towards said beam dump.

* * * * *